US007393646B2

(12) United States Patent
Hurst et al.

(10) Patent No.: US 7,393,646 B2
(45) Date of Patent: Jul. 1, 2008

(54) METHOD, APPARATUS AND SYSTEM FOR QUANTIFYING THE CONTENT OF GENETICALLY MODIFIED MATERIAL IN A SAMPLE

(75) Inventors: Maurice Hurst, Eden Prairie, MN (US); Randal Giroux, Chaska, MN (US)

(73) Assignee: Cargill, Inc., Minneapolis, MN (US)

( * ) Notice: Subject to any disclaimer, the term of this patent is extended or adjusted under 35 U.S.C. 154(b) by 0 days.

(21) Appl. No.: 11/453,557

(22) Filed: Jun. 15, 2006

(65) Prior Publication Data

US 2007/0015186 A1 Jan. 18, 2007

Related U.S. Application Data

(60) Provisional application No. 60/692,285, filed on Jun. 20, 2005.

(51) Int. Cl.

| | |
|---|---|
| ***C12Q 1/68*** | (2006.01) |
| ***G01N 33/53*** | (2006.01) |
| ***C07H 21/02*** | (2006.01) |
| ***C07H 21/04*** | (2006.01) |

(52) U.S. Cl. .......................... 435/6; 435/7.1; 536/23.1; 536/24.3

(58) Field of Classification Search ..................... 435/6, 435/7.1; 536/23.1, 24.3

See application file for complete search history.

(56) References Cited

U.S. PATENT DOCUMENTS

| | | | | |
|---|---|---|---|---|
| 2002/0056147 | A1 * | 5/2002 | Dau et al. | 800/8 |
| 2002/0132271 | A1 * | 9/2002 | Onisk et al. | 435/7.4 |
| 2003/0059803 | A1 * | 3/2003 | Werner et al. | 435/6 |
| 2006/0019251 | A1 * | 1/2006 | Hormisch | 435/6 |
| 2007/0077561 | A1 * | 4/2007 | Hong | 435/6 |
| 2007/0117106 | A1 * | 5/2007 | Remacle et al. | 435/6 |

FOREIGN PATENT DOCUMENTS

| | | | |
|---|---|---|---|
| EP | 1780291 A1 | * | 2/2007 |
| WO | WO00/47764 | * | 8/2000 |

OTHER PUBLICATIONS

Aarts et al., Traceability of Genetically Modified Organisms. Expert Review of Molecular Diagnostics 2(1) : 69-76 (Jan. 2002).*

Degrieck et al., Quantitative GMO detection in maize (*Zea mays* L.) seed lots by means of a three-dimensional PCR based screening strategy. Seed Science & Technology 33:31-43 (Jan.-Feb. 2005).*

Akiyama et al., Quantitative detection system for maize sample containing combined-trait genetically modified maize. Analytical Chemistry 77 : 7421-7428 (Nov. 2005).*

Lipp et al. , Validation of a method based on polymerase chain reaction for the detection of genetically modified organisms in various processed foodstuffs. Eur. Food Res Technol. 212 : 497-504(2001).*

Holst-Jensen et al., PCR technology for screening and quantification of genetically modified organisms (GMOs). Anal. Bioanal. Chem. 375 : 985-993 (2003).*

Germini et al. Development of a seven-target multiplex PCR for the simultaneous detection of transgenic soybean and maize in feeds and foods. J. Agric. Food Chem. 52 : 3275-3280 (2004).*

Hernandez et al. , A rapeseed-specific gene, acetyl-CoA Carboxylase, can be used as a reference for qualitative and real-time quantitative PCR detection of transgenes from mixed food samples. J. Agric. Food Chem. 49 : 3622-3627(2001).*

Petit et al., Characterization of genetically modified maize in weakly contaminated seed batches and identification of the origin of the adventitious contamination. J. of AOAC International 90 (4) : 1098-1106 (2007).*

Lipp et al., Polymerase chain reaction technology as analytical tool in agricultural biotechnology. J. of AOAC International 88 (1) : 136-155 (2005).*

Middleton et al., DNA extraction from bulked samples of canola seed and the use of multiplex PCR for detection of adventitious contamination with genetically modified seed. Seed Science & Technology 31 : 487-495(2003).*

Notification of Transmittal of the International Search Report and the Written Opinion of the International Searching Authority for corresponding patent application No. PCT/US2006/023440, 15 pages, mailed Oct. 11, 2006.

MAICh, (Mediterranean Agronomic Institute of Chania) "Laboratories-GMO Testing Laboratory", XP-002398910, (1 page) http://www.maich.gr/resources/laboratories/gmo.html 2003.

BIO-RAD: "GMO Testing in Food and Feed," XP002398909, 8 pages, http://www.bio-rad.com Feb. 2005.

Holst-Jensen, Arne et al., "PCR technology for screening and quantification of genetically modified organisms (GMOs)," Analytical and Bioanalytical Chemistry, vol. 375: pp. 985-993, XP002398908, 9 pages, 2003.

Kay, "Comparison of sampling approaches for grain lots", European Commission Directorate General JRC, Institute for Health and Consumer Protection (IHCP), XP002398907, 14 pages. http://www.biotech.jrc.it/home/doc/sampling_comparison_Kay_paper.pdf Feb. 23, 2001.

Miraglia et al., "Detection and traceability of genetically modified organisms in the food production chain," Food and Chemical Toxicology, vol. 42: pp. 1157-1180, XP002398906, 24 pages, Feb. 4, 2004.

(Continued)

*Primary Examiner*—Ethan Whisenant
(74) *Attorney, Agent, or Firm*—Paula A. DeGrandis; Klarquist Sparkman, LLP

(57) ABSTRACT

A method including providing an initial test sample including a primary material and a relatively smaller amount of at least one adventitious material; combining the initial test sample with a standard addition of at least one adventitious material to form a final test sample, wherein the standard addition has a known amount of genetically modified adventitious material; and analyzing the final test sample to determine the % GMO of the primary material and the % GMO of the adventitious material.

9 Claims, 2 Drawing Sheets

OTHER PUBLICATIONS

Genetic ID, Inc.: "Genetic ID's Analytical Methods for Detection and Quantification of Genetically Modified Organisms in Foods and Agricultural Products," XP002398905, 26 pages; http://www.foe.org/camps/comm/safefood/getfood/foodaid/testing_protocol_2-2.pdf Apr. 2001.

Kay et al., "Sampling Strategies for GMO Detection and/or Quantification", European Commission Directorate General JRC, XP002398904, 17 pages. http://www.biotech.jrc.it/home/doc/euroreport-sampling_strategies.pdf Nov. 2001.

Heinemann et al., "Is confidence in the monitoring of GE foods justified?", Trends in Biotechnology, vol. 22, No. 7, XP002398904, 6 pages, Jul. 2004.

Anklam et al., "Analytical methods for detection and determination of genetically modified organisms in agricultural crops and plant-derived food products", European Food Research and Technology, vol. 214, pp. 3-26, XP0022248185, 24 pages, 2002.

Straub et al., "Limits of a PCR-based detection method for genetically modified soya beans in wheat bread production", Springer-Verlag, Z Lebensm Unters Forsch A, vol. 208, pp. 77-82; XP001009571, 6 pages, 1999.

Stram et al., "Detection of Residues of Genetically Modified Soybeans in Breaded Fried Turkey Cutlets", Journal of Food Science, vol. 65, No. 4, 3 pages, 2000.

* cited by examiner

METHOD, APPARATUS AND SYSTEM FOR QUANTIFYING THE CONTENT OF GENETICALLY MODIFIED MATERIAL IN A SAMPLE

This application claims the benefit of U.S. provisional application No. 60/692,285, filed Jun. 20, 2005, the entire content of which is incorporated herein by reference.

TECHNICAL FIELD

This disclosure relates to a method for accurately determining the percentage by weight of genetically modified material (% GMO) in a sample of a material.

BACKGROUND

Many countries around the world, including the United States, the European Union, Japan, and Korea, regulate the percentage by weight amount of genetically modified material (% GMO) that may be present in imported agricultural goods. In a shipment of imported agricultural goods such as, for example, corn, soybeans wheat, canola and the like, the European Union currently allows a maximum of 0.9% by weight of GMO, while Japan currently allows no more than 5%, and Korea currently imposes a limit of 3%.

When an agricultural material is harvested from a farmer's field and loaded onto a truck for shipment to a supplier, a rapid protein test is often performed on a sample of the material to determine the approximate % GMO therein. Assuming that the rapid protein test determines the % GMO of the sample is less than the required tolerance, the agricultural material is then shipped and stored temporarily in a silo before being offloaded onto a barge or other conveyance for shipment to a final destination (e.g., an ocean port).

A sample of the agricultural material is often submitted to a testing laboratory, which performs on the sample a PCR or other suitable DNA test, since this type of testing is often the official regulatory test recognized by the country designated to receive the shipment. The PCR test purports to accurately determine the % GMO present in the sample. The most common PCR test, generally known as the 35S test, evaluates the agricultural material to detect the presence of common genetic elements found in most events and allows for screening of the material.

In the PCR test, the sample is ground and genetic material is extracted. Screening tests are performed on the extracted genetic material to detect the presence of specific genetic elements, such as the 35S promoter or other specific genetic elements. Each type of agricultural material such as, for example, corn, soybeans, canola, and wheat, have specific promoters detected by the PCR screening process. For example, in a corn sample the standard 35S test screens for up to 7 specific corn promoters, and the amount of each promoter detected is summed to determine the number of transgenes in the sample. The number of transgenes is then divided by the number of control (non-genetically modified) genes in the sample to determine the percentage by weight of genetically modified material (% GMO).

SUMMARY

In one aspect, this disclosure is directed to a method for determining the percentage by weight of genetically modified material in an original test sample containing an excess of a primary material and a relatively smaller amount of at least one adventitious material. In this method a known amount of at least one adventitious material, referred to herein as a standard addition, is combined with the original test sample to form a final test sample. The standard addition includes a known amount of genetically modified material, and is preferably substantially free of genetically modified material. Suitable analytical techniques are then applied to the final test sample to determine the % GMO of the primary material and the % GMO of the adventitious material.

In another aspect, this disclosure is directed to an apparatus for determining the percentage by weight of genetically modified material in an original test sample including a primary material and a relatively smaller amount of at least one adventitious material. The system determines the presence of each adventitious material in the original test sample, selects an amount of a standard addition for each adventitious material, and combines the adventitious material(s) with the original test sample to form a final test sample. The apparatus then analyzes the final test sample using suitable PCR or other DNA analysis techniques and determines the % GMO of the first material and the % GMO of at least one adventitious material.

In a preferred embodiment, the analytical apparatus includes a digital computer that computes the % GMO of the first agricultural material and the % GMO of the adventitious material. The computer then outputs the % GMO of the first agricultural material and the % GMO of the adventitious material, stores the % GMO values in a database, and displays the % GMO values on a suitable display device for a user.

In yet another embodiment, this disclosure is directed to a computer-readable medium containing instructions. The instructions cause a programmable processor to extract from a database or spreadsheet: the number of transgenes of a primary material in the final sample; and the number of non-genetically modified control genes of the primary material in the final sample; and then calculate % GMO of the primary material in the final sample. The instructions also cause the programmable processor to extract from a database or spreadsheet: the number of transgenes of the at least one adventitious material in the final sample; and the number of non-genetically modified control genes of at least one of the adventitious materials in the final sample; and then calculate the % GMO of the adventitious material(s) in the final sample. The calculated % GMO may then be displayed on an appropriately designed user interface, stored in a database, or output to a suitable peripheral device.

In yet another embodiment, the disclosure is directed to a system for monitoring the content of genetically altered material, % GMO, in an agricultural commodity using the processes and apparatus described herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
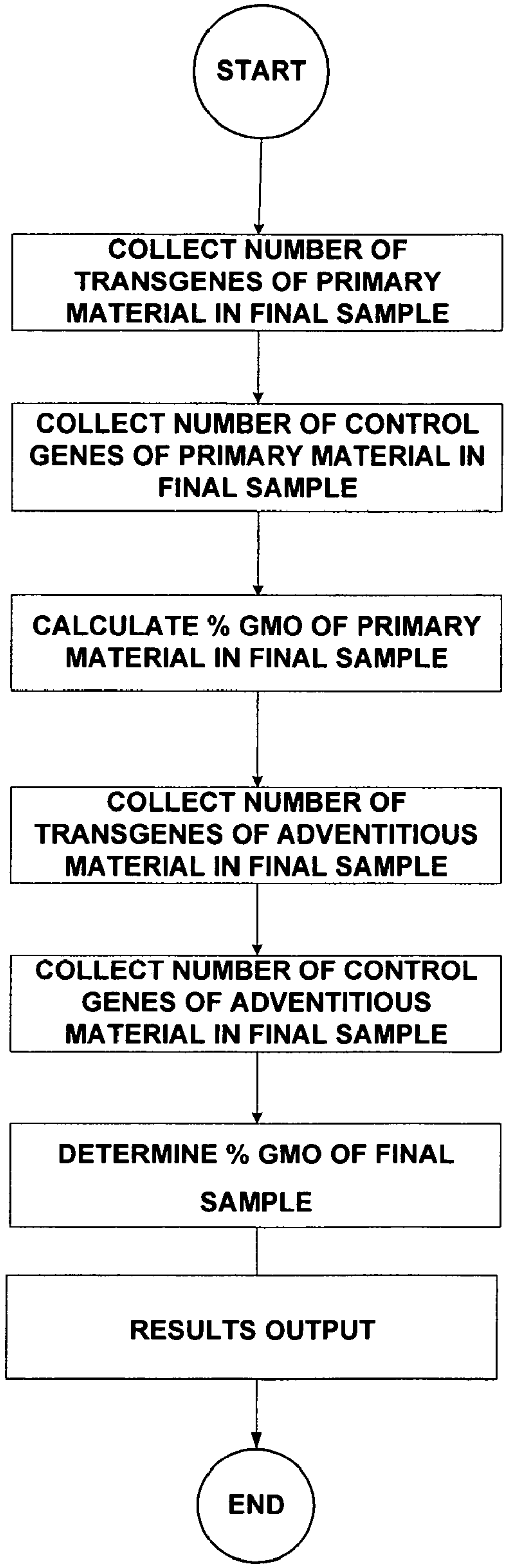
FIG. 1 is a flow chart illustrating operation of an exemplary apparatus implementing the process described in the present disclosure.

The results of the PCR test are typically available about 2 days after a sample of an agricultural material is received at the testing laboratory. By the time the results are available for a particular shipment of the agricultural material, that shipment is well on its way to a final destination (e.g., an ocean port), or has already been loaded on a cargo ship for transport to a designated country. If the results of the DNA screening test such as, for example, PCR, for the shipment fail to comply with the regulations in the designated country, the shipment must be offloaded from the cargo ship or diverted to another destination. Of course, this delays the originally planned shipment and increases costs for the supplier of the agricultural commodity. Therefore, to ensure regulatory compliance and effectively characterize the supply chain for a particular agricultural material, the supplier must ensure that the PCR test for a particular agricultural material is accurate.

Conventional PCR testing assumes that the sample of agricultural material tested is pure. However, all shipments of materials of a particular type, referred to herein as primary materials, usually contain an amount of at least one agricultural material of another type, which is referred to herein as an adventitious material. The amount of the adventitious material in a sample of a material may vary widely, but the adventitious material is typically present at a relatively low level compared to the amount of the primary material in the sample. For example, the adventitious material makes up less than about 5% by weight of the sample of the primary material, preferably less than about 1%, more preferably less than about 0.5%, and most preferably less than about 0.1%.

For example, a shipment of corn typically includes a small amount (less than about 0.5% by weight) of another adventitious grain, such as soybeans. The adventitious material may be introduced into the shipment at any point in the supply chain—in a field where the corn is harvested, in a truck while the corn is transported to a silo, in the silo, on a barge, or on a cargo ship. If the adventitious material is genetically modified, its transgenes are extracted and detected by the standard PCR test. Therefore, the additional genetically modified material from an impurity can have a significant impact on the calculation of the % GMO of the entire sample.

For example, in a pure sample of 100 corn kernels, if 1 corn kernel is genetically modified, the sample is 1% by weight GMO (1% GMO). In the PCR test procedure, the ground corn sample is analyzed to determine the presence of promoters specific to corn, and the total number of promoters detected is summed to determine the number of transgenes in the sample. As shown in Formula I, the % GMO is determined by dividing the number of detected transgenes specific to corn by the number of control corn genes in the sample:

% GMO (corn)=[# of corn transgenes]/[# of control corn genes] (Formula I)

This calculation is typically accurate since the number of control corn genes is significantly larger than the number of transgenes in the sample.

However, if 0.5% by weight of genetically modified soybeans is added to the sample to represent the presence of an adventitious grain of another type, the standard PCR test evaluates the % GMO of the corn, but does not account for the transgenes contributed by the soybeans (Formula II):

% GMO (corn)={[# of soybean transgenes]+[# of corn transgenes]}/[# of control corn genes] (Formula II)

% GMO (total)=[% GMO (corn)]+[% GMO (soybeans)] (Formula III)

According to Formula III, the % GMO (total) is expected to be 1.0%+0.5%=1.5%. If this theoretical calculation of % GMO is accurate, the % GMO contribution of the adventitious presence can be calculated by simply subtracting the % GMO value for the major commodity from the total % GMO value. If the theoretical calculation is not appropriate to determine the adventitious presence, the analyst must calculate the % GMO of the adventitious grains directly.

To determine the contribution of the adventitious presence in the sample, in this case soybeans in a corn sample, since the number of control soybean genes in the sample is relatively small, the ability of the analyst to accurately calculate the % GMO (soybeans) is unlikely to be possible since the denominator for the % GMO (soybeans) is too small to be statistically significant. As such, the value calculated using Formulas II and III provides a % GMO (total) that is incorrect and does not accurately account for the % GMO contributed by the adventitious (soybean) presence. Since the % GMO (soybeans) value determined using Formulas II and III is neither accurate nor reproducible, as a result the amount of genetically modified soybean material in the sample is in effect non-quantifiable.

Therefore, to ensure regulatory compliance and effectively characterize the supply chain for a particular agricultural material, the supplier must ensure that the determination of % GMO for the material is accurate. The amount of genetically modified material resulting from the presence of one or more adventitious materials in a shipment of a primary material is not generally quantifiable using conventional PCR methods of analysis, which leads to inaccurate characterization of the % GMO of the entire shipment. An analytical technique is needed to provide a more accurate measure of the percent by weight of genetically modified material in a sample of a primary material containing adventitious materials or relatively small amounts of other materials.

In one aspect, this disclosure describes a process that provides a more accurate determination of the % GMO of a shipment that includes a primary material and a relatively small amount of at least one adventitious material. The process is particularly well suited to analysis of agricultural materials such as, for example, grains and oilseeds, but its application is not limited to such materials.

In this process, an initial test sample is extracted from the shipment that includes a primary material and a relatively smaller amount of at least one adventitious material.

The % GMO of a test sample is calculated using Formula IV:

% GMO (total)=[% GMO (primary materials)]+Σ{[% GMO (adventitious materials)]} (Formula IV)

The % GMO of the primary material in a test sample is determined using the standard PCR procedure:

% GMO (primary)=[# of primary transgenes]/[# of control primary genes] (Formula V)

The % GMO of the adventitious materials in a test sample is determined by Formula VI:

% GMO (adventitious)=Σ{[# of adventitous transgenes]/[# of control adventious genes]} (Formula VI)

To ensure that Formula VI returns an accurate value for the % GMO of the adventitious materials in a test sample, an additional amount of at least one, preferably each, adventitious material is added to the initial test sample individually or in composite to form a final test sample. This additional amount of adventitious material, referred to herein as a standard addition, increases the amount of extractable species specific DNA of each adventitious grain and/or oilseed type such that an accurate value of % GMO is returned for each adventitious material present in the final test sample. The amount of standard addition for each adventitious material will vary widely depending on the circumstances, but the standard addition should be added to the initial test sample in an amount sufficient for each adventitious material such that the number of control adventitious genes in Formula VI is sufficiently large to provide an accurate and reproducible value for the % GMO of the adventitious material in the final test sample. Typically, the amount of sample addition for each adventitious material should be sufficiently large such that the number of control adventitious genes is present in excess compared to the number of transgenes detectable for the adventitious material in the final test sample.

The sample addition for each adventitious material should have a known amount of genetically modified material. If the sample addition includes any genetically modified material, the amount of genetically modified material in Formula VI is preferably adjusted accordingly to ensure accuracy and reproducibility. Preferably, to make the calculations as simple and as accurate as possible, the sample addition preferably will be substantially free of genetically modified material, and most preferably completely free of genetically modified material.

The standard addition for each adventitious material should be ground and added to the initial test sample to form the final test sample prior to the DNA extraction portion of the PCR analysis procedure. The final test sample is then tested using conventional DNA extraction and analysis techniques, typically PCR analysis, to determine the % GMO according to Formula IV.

For example, if corn is the primary agricultural material in a cargo and soybeans are also present as an impurity or are introduced into the sample at some point in the supply chain, the initial sample to be analyzed for % GMO content includes corn and a relatively smaller amount of soybeans. In this example, a standard addition of soybeans, preferably non-GMO soybeans, should be ground and added to the initial test sample to form a final test sample prior to the DNA extraction and PCR analysis.

The process described in this disclosure can be utilized to test samples of any commodity, preferably agricultural commodities or grain and/or oilseed products, at any point in the supply or distribution chain.

The process may be performed at any analytical laboratory suitably equipped for DNA extraction and testing such as PCR, or may be implemented by a suitable analytical apparatus. For example, the apparatus determines the presence of each adventitious material in the original test sample, selects an amount of a standard addition for at least one of the adventitious materials, and combines the adventitious material(s) with the initial test sample to form the final test sample. The apparatus then analyzes the final test sample using suitable DNA extraction and conventional analysis techniques and determines the % GMO of the primary material and the % GMO of the adventitious material using the above-described process.

Referring to FIG. 1, in a preferred embodiment, the analytical apparatus includes a digital computer that operates according to the flow diagram 1 and computes the % GMO of the first agricultural material and the % GMO of the adventitious material. The computer then outputs the % GMO of the first agricultural material and the % GMO of the adventitious material, stores the % GMO values in a database, and displays the % GMO values on a suitable display device for a user.

In another embodiment, this disclosure is directed to a computer-readable medium containing instructions that cause a programmable processor to extract from a database or spreadsheet the number of transgenes of the primary material in the final sample; and the number of non-genetically modified control genes of the primary material in the final sample; and then determine the % GMO of the first agricultural material in the final sample. The instructions also cause the programmable processor to extract from a database or spreadsheet: the number of transgenes of the adventitious material in the final sample; and the number of non-genetically modified control genes of the adventitious material in the final sample; and then determine the % GMO of the adventitious material in the final sample. The calculated % GMO may then be displayed on an appropriately designed user interface, stored in a database, or outputted to a suitable peripheral device.

Figure 2:
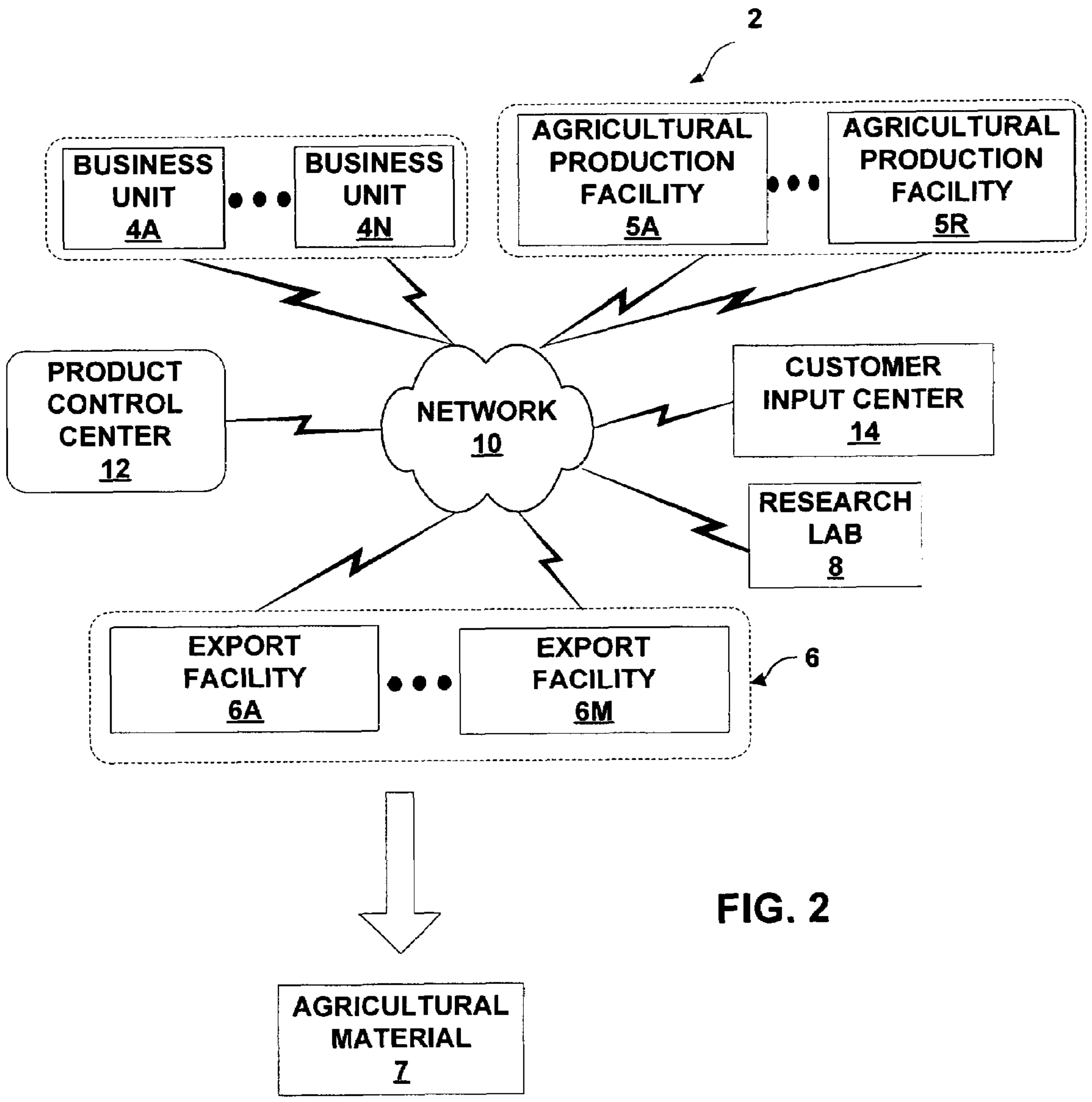
FIG. 2 is a block diagram illustrating a system for monitoring the genetically modified content of products using the processes and apparatus described in the present disclosure.

In yet another embodiment, the process described in this disclosure may also be implemented as part of a commodity distribution system. FIG. 2 is a block diagram illustrating a system 2 for determining the % GMO of a shipment of an agricultural material and tracking the agricultural material as it moves along the supply chain to its export destination.

More specifically, a product control center 12 maintains a data model that correlates genetic test data for a shipment of an agricultural material 7 with regulatory requirements for particular export markets. The agricultural material 7 may be any animal or vegetable product, for example, grains such as corn, soybeans, wheat, cotton, canola and the like, or animal products such as, for example, beef, pork, chicken or fish.

Remote export facilities 6 communicate with the product control center 12 via a network 10 to retrieve specific genetic test and regulatory data regarding the agricultural material 7. The remote export facilities 6 closely monitor the genetic composition of a particular shipment of the agricultural material 7 to ensure the material 7 satisfies import requirements for the its final destination.

A research lab 8 interacts with the product control center 12 and a business unit 4 to generate genetic information for planned and ongoing shipments of the agricultural material 7. Initially, research lab 8 develops the testing protocols, preferably utilizing the apparatus and processes described herein, for determining the genetic makeup and content of agricultural materials 7 grown or produced by a collection of agricultural production facilities 5. Once the research lab 8 has developed the test protocol, the research lab 8 communicates the protocol to the product control center 12. The agricultural production and storage facilities 5 communicate with the product control center 12 to select desired genetic properties for the agricultural material 7 produced by the production/storage facilities 5.

The business units 4 may, for example, direct the production facilities 5 to produce agricultural materials having different performance properties based on pricing, customer preference information received from customer input center 14, current inventory, current sales volumes, geographic preferences or other strategic business information. The business units 4 may, for example, interact with product control center 12 to direct production facilities 6 to produce products within various ranges of performance, thereby lending to a tiered pricing scheme. In addition, the product control center 12 supports and facilitates "on-demand" supply of agricultural material 7 having a precise genetic makeup or performance property. By streamlining the delivery of genetic data to such export facilities 6 when needed, business units 4 can direct production/storage facilities 5 to produce and/or supply products when inventory levels dictate, thereby allowing the company to satisfy any "just-in-time" supply contracts and other business relationships.

In general, authorized users of business units 4, research lab 8 and customer input center 14 interact with product control center 12 via network 10 to develop and update the genetic testing protocols and databases, as well as to provide strategic business information to control the supply and distribution of the agricultural material 7. Each user typically interacts with a computing device suitable for communication and interaction with product control center 12 via network 10. For example, a user may use a workstation, personal computer, laptop computer, or even a personal digital assistant (PDA) such as a Palm™ organizer from Palm Inc. of Santa Clara, Calif. or Windows CE device. The communication device executes communication software, typically a web browser such as Internet Explorer™ from Microsoft Corporation of Redmond, Wash., in order to communicate with product control center 12. Network 10 represents any communication link suitable for communicating data, such as a wide-area network, local area network, or a global computer network like the World Wide Web.

The invention will now be described with reference to the following non-limiting examples.

EXAMPLE

A barge NL173 containing a shipment of corn was first submitted for 35S GMO testing on Oct. 25, 2004, and the result of the analysis for the total % GMO of the shipment was 5.9%. This % GMO result was inconsistent with the lateral flow strip threshold test performed prior to loading the grain on the barge, which returned a % GMO value of less than about 3%.

To understand the corn events contributing to this high GMO result, additional tests were performed on the sample. The sample was first tested for the presence of Ga21 (another corn event not evaluated in the original 35S test), but no GA21 was detected in the corn sample. The samples were then tested for the presence of events that do not express the protein at high level and may have been missed by lateral flow strip testing (Bt176 and Mon810). These samples were tested and these events contributed less than 1.7% of the detected GMO level.

The samples were then tested for the presence of the NK603 event, which is known to be grown in high concentrations in the draw area. The NK603 event was found to contain 0.7% GMO to the total % GMO value.

When the corn % GMO values were added together, these events contributed 2.4% of the total GMO content of 5.9%.

Because these two numbers were inconsistent, it was suspected that the sample may contain GMO soybeans and that this was contributing to the total % GMO test result. The sample was then analyzed qualitatively and tested positive for the presence of GMO soybeans.

Once the presence of GMO soybeans was confirmed, the samples were re-tested using a standard addition of non-GMO soybean material, and the % GMO of the sample was found to be 2.4%.

The validity of the standards addition approach was then confirmed using previously tested samples having known % GMO content.

Various embodiments of the invention have been described, and these and other embodiments are within the scope of the following claims.

The invention claimed is:

1. A method comprising:

providing an initial test sample comprising a primary material and a relatively smaller amount of at least one adventitious material;

combining the initial test sample with a standard addition of at least one adventitious material to form a final test sample, wherein the standard addition has a known amount of genetically modified adventitious material; and analyzing the final test sample to determine the % GMO of the primary material and the % GMO of the adventitious material.

2. The method of claim 1, wherein the standard addition is free of genetically modified adventitious material.

3. The method of claim 1, wherein the analyzing step (c) comprises applying a DNA extraction and PCR analysis to the final test sample.

4. The method of claim 1, wherein the original test sample comprises an excess of the primary material.

5. The method of claim 1, wherein the primary material comprises an agricultural material.

6. The method of claim 5, wherein the agricultural material comprises a grain.

7. The method of claim 6, wherein the grain is selected from the group consisting of corn, soybeans, canola and wheat.

8. The method of claim 5, wherein the adventitious material comprises soybeans.

9. The method of claim 1, wherein the primary material is corn and the adventitious material is soybeans.

* * * * *